United States Patent [19]

Caskey et al.

[11] Patent Number: 4,571,437

[45] Date of Patent: * Feb. 18, 1986

[54] PROCESS FOR PREPARING P-AMINOPHENOL AND ALKYL SUBSTITUTED P-AMINOPHENOL

[75] Inventors: Douglas C. Caskey, O'Fallon; Douglas W. Chapman, St. Louis, both of Mo.

[73] Assignee: Mallinckrodt, Inc., St. Louis, Mo.

[*] Notice: The portion of the term of this patent subsequent to Nov. 15, 2000 has been disclaimed.

[21] Appl. No.: 516,857

[22] Filed: Jul. 25, 1983

Related U.S. Application Data

[63] Continuation-in-part of Ser. No. 343,996, Jan. 29, 1982, abandoned.

[51] Int. Cl.$^4$ .............................................. C07C 89/00
[52] U.S. Cl. ..................................... 564/418; 564/300
[58] Field of Search ......................................... 564/418

[56] References Cited

U.S. PATENT DOCUMENTS

| | | | |
|---|---|---|---|
| 3,383,416 | 5/1968 | Benner | 260/575 |
| 3,654,365 | 4/1972 | Daunis et al. | 260/575 |
| 3,694,509 | 9/1972 | Rylander et al. | 260/578 |
| 3,715,397 | 2/1973 | Rylander et al. | 260/575 |
| 3,953,509 | 4/1976 | Greco | 260/580 |
| 4,176,138 | 11/1979 | Sathe | 260/575 |
| 4,307,249 | 12/1981 | Derrenbacker | 564/418 |

FOREIGN PATENT DOCUMENTS 54-24837  2/1979  Japan .................................... 564/418

OTHER PUBLICATIONS

Svidchenko et al., U.S.S.R. 523081, *Chem. Abstracts* 85:1428162z.

Mahadeo Indian patent 140158, *Chem. Abstracts* 92:94060u.

*Primary Examiner*—Charles F. Warren
*Assistant Examiner*—Harry B. Shubin
*Attorney, Agent, or Firm*—Senniger, Powers, Leavitt and Roedel

[57] ABSTRACT

A process for preparing unsubstituted and alkyl substituted p-aminophenols. A charge mixture is prepared comprising an unsubstituted or alkyl substituted nitrobenzene, a highly dissociated acid, a catalyst containing platinum and a divalent sulfur compound in which sulfur is bonded to two other moieties, the sulfur compound being present in a proportion of between about 0.1 and about 100 moles per gram-atom of platinum. The mixture comprises an organic phase containing the substrate and an aqueous phase containing the acid. Hydrogen is introduced into the mixture at a pressure of 0-50 psig while the mixture is agitated at a temperature of 70° C. to 100° C., thereby causing the substrate to be reduced to phenylhydroxylamine or an alkyl substituted phenylhydroxylamine. The hydroxylamine is rearranged in the presence of acid to the substituted or unsubstituted p-aminophenol, which is recovered from the aqueous phase.

18 Claims, 1 Drawing Figure

PROCESS FOR PREPARING P-AMINOPHENOL AND ALKYL SUBSTITUTED P-AMINOPHENOL

CROSS-REFERENCE TO RELATED APPLICATION

This application is a continuation-in-part of Ser. No. 343,996 filed Jan. 29, 1982 now abandoned.

BACKGROUND OF THE INVENTION

This invention relates to the field of the preparation of p-aminophenol and, more particularly, to an improved process for the manufacture of p-aminophenol by catalytic hydrogenation.

Various processes are known to the art for the manufacture of p-aminophenol. In the process described in Benner U.S. Pat. No. 3,383,416, nitrobenzene is catalytically hydrogenated in the presence of a dilute sulfuric acid solution. Under the conditions utilized in the Benner patent, nitrobenzene is subject to complete reduction to aniline by reaction with three moles of hydrogen.

However, the intermediate phenylhydroxylamine, produced by reaction of nitrobenzene with two moles of hydrogen, is rapidly removed from the reaction zone by absorption into the sulfuric acid phase where it rearranges to p-aminophenol:

Fortuitously, the noble metal catalyst tends to congregate in the nitrobenzene phase so that phenylhydroxylamine absorbed into the acid phase is essentially removed from the hydrogenation reaction zone, and conversion of phenylhydroxylamine to aniline is thereby inhibited. This feature also permits recovery of the catalyst in the nitrobenzene phase when the phases are permitted to separate so that, by terminating the reaction prior to the conversion of all the nitrobenzene, the catalyst is easily recovered by decantation and recycled in its nitrobenzene vehicle for use in another batch, or in an earlier stage of a cascade continuous hydrogenator.

Despite its numerous salutary features, the Benner process does not entirely avoid conversion of phenylhydroxylamine to aniline. Thus, typically the yield of p-aminophenol is about 75% while 15% of the nitrobenzene is reduced to aniline. The amount of by-product aniline obtained can be minimized by lowering the reaction rate, but this, of course, involves a sacrifice in productivity.

Rylander et al. U.S. Pat. No. 3,715,397 discloses a process for preparation of p-aminophenol by catalytic hyrogenation of nitrobenzene using a platinum oxide catalyst in the presence of sulfuric acid and dimethyl sulfoxide. Phenylhydroxylamine produced in the hydrogenation is absorbed into the acid phase and converted in situ to p-aminophenol. The acid strength is that obtained by mixing 25 ml. concentrated sulfuric acid with 75 ml. water. Reaction is carried out in a batch system until absorption of two moles of hydrogen per mole of nitrobenzene. According to the Rylander et al. disclosure, the reaction may be carried out over a wide range of temperatures, with room temperature apparently being preferred.

In the co-pending and co-assigned application of Thomas H. McFadden, Ser. No. 343,997, a process is described in which dimethyl sulfoxide or another organic sulfoxide is incorporated into a continuous process for the manufacture of p-aminophenol by catalytic hydrogenation of nitrobenzene. In the McFadden process, 50 to 90 percent of the nitrobenzene charged to the first of three cascade hydrogenators is reduced leaving an unreacted, nitrobenzene fraction which is allowed to separate from the reaction mixture and in which the catalyst congregates. After separation, the nitrobenzene phase containing the catalyst is recycled to the first hydrogenator.

SUMMARY OF THE INVENTION

Among the several objects of the present invention, may be noted the provision of an improved process for the manufacture of p-aminophenol or alkyl substitued p-aminophenols by catalytic hydrogenation of nitrobenzene or an alkyl substituted nitrobenzene; the provision of such a process which minimizes the formation of by-product aniline; the provision of such a process which facilitates production of substituted or unsubstituted p-aminophenol in high yield and at high productivity; the provision of such a process which improves the selectivity of the catalyst for p-aminophenol and which inhibits formation of by-product aniline by addition of relatively low proportions of catalyst modifiers; and the provision of such a process which provides improved catalytic activity without adverse effect on the partial pressure of hydrogen available for driving the reduction reaction.

Briefly, therefore, the present invention is directed to a process for preparation of a substituted or unsubstituted p-aminophenol having the formula:

where R is lower alkyl and n is 0, 1 or 2. The process comprises preparing a charge mixture comprising a substituted or unsubstituted nitrobenzene substrate having the formula:

where R and n are as defined above, a highly dissociated acid, a catalyst containing platinum, and a sulfur compound. The sulfur compound is one in which divalent sulfur is bonded to two other moieties, and it is present in a proportion of between about 0.1 and about 100 moles per gram-atom platinum. The mixture comprises an organic phase containing the substrate and an aqueous phase containing the acid. Hydrogen is introduced into the mixture at a pressure of between about 0 and about 50 psig while the mixture is agitated at a temperature of between about 70° and about 100° C., thereby causing the substrate to be reduced to an intermediate comprising a substituted or unsubstituted phenylhydroxylamine having the structural formula:

where R and n are as defined above. The intermediate is rearranged in the presence of the aforesaid acid to produce p-aminophenol or an alkyl substituted p-aminophenol corresponding to the substrate. The product is recovered from the aqueous phase.

BRIEF DESCRIPTION OF THE DRAWINGS

The single FIGURE of the drawings is a schematic flow sheet illustrating an embodiment in which the process of the invention is carried out continuously in a cascade hydrogenator system.

DESCRIPTION OF THE PREFERRED EMBODIMENTS

In accordance with the present invention, it has been discovered that improvements in productivity and yield may be achieved by using a divalent sulfur compound to modify the catalyst system used in the preparation of p-aminophenol by hydrogenation of nitrobenzene in the presence of a highly dissociated acid. Use of a sulfur compound in such a system essentially eliminates conversion of nitrobenzene to byproduct aniline, and thus enhances both the yields and productivity achievable in the hydrogenation process. Yield improvement is realized not only with respect to the substrate, but also with respect to consumption of hydrogen.

Use of a sulfur compound catalyst modifier allows application of higher hydrogen pressures than those permitted by the Benner process and thus affords opportunity for higher productivities. In the Benner process, pressures in excess of 5 psig favor aniline formation and are, thus, preferably avoided. In the process of the invention, the use of a sulfur compound inhibits aniline formation and allows operation at pressures up to 50 psig or higher.

It has been further found that divalent sulfur compounds in which sulfur is bonded to two other moieties provide more effective catalyst selectivity enhancement than does the dimethyl sulfoxide taught by Rylander et al. While the charge mixture may contain between about 0.1 and 100 moles sulfur compound per gram atom of platinum, normally a proportion in the lower end of that range is fully adequate for achieving the desired catalyst selectivity.

Among the various sulfur compounds which can be used in the process of the invention are dialkyl sulfides, diaryl sulfides, dialkyl disulfides, aryl alkyl sulfides, thiophene, substituted thiophenes, thiophane, substituted thiophanes, aliphatic thiols, aromatic thiols, methionine and hydrogen sulfide. It is strongly preferred that the sulfur compound be substantially nonvolatile, i.e., that, under the conditions of the hydrogenation reaction, volatility not be such as to lower the hydrogen partial pressure so much as to adversely affect productivity. Although, by this criterion the suitability of the particular sulfur compounds may vary with the total available hydrogen pressure, it is particularly preferred that the sulfur compound used be one which causes no penalty in productivity in a continuous system at an available hydrogen pressure of 50 psig. Generally, results are satisfactory if the sulfur compound has an atmospheric boiling point not lower than the temperature at which the hydrogenation is conducted.

While the partial pressure of sulfide compound in the vapor space of the hydrogenator varies with the proportion of sulfide compound in the reacting mixture, it has been found that the vapor pressure of dimethyl sulfide is high enough to inhibit reaction at 80° C. where the total available hydrogen pressure is in the 50 psig range. Thus, dimethyl sulfide, hydrogen sulfide and other relatively volatile sulfur compounds are preferably avoided, even though they are effective for the purpose for enhancing the selectivity of the catalyst. Diethyl sulfide has a volatility low enough to be satisfactory in most circumstances, while diisopropyl sulfide and di(n-butyl) sulfide have even lower vapor pressures and are highly suitable.

To minimize partial pressure of sulfur compound in the vapor space, it is particularly preferred that the divalent sulfur compound utilized have an atmospheric boiling point of at least 80° C. and thus be essentially non-volatile under the conditions prevailing in the catalytic hydrogenation of nitrobenzene to p-aminophenol. To minimize formation of by-products, it is preferred that the compound used be hydrolytically stable under the hydrogenation reaction conditions and, in particular, that it be stable at temperatures in the range of 80° C. to 100° C. It is also preferred, that in the two liquid phases of the hydrogenation system, the sulfur compound be distributed predominantly to the aqueous acid phase rather than the organic nitrobenzene phase. Additionally, it is preferred that the sulfur compound be unreactive with either arylhydroxlyamine or the mineral acid used for the rearrangement reaction. Accordingly, divalent sulfur compounds such as hydrogen sulfide and various mercaptans, which are otherwise effective catalyst modifiers but tend to react with phenylhydroxylamine, are preferably avoided.

A preferred catalyst modifying compound is methionine. Other preferred sulfur compounds include alkylthiobenzenesulfonic acids such as p-methylthiobenzenesulfonic acid, m-ethylthiobenzenesulfonic acid, and m-butylthiobenzenesulfonic acid; ring substituted alkylthiobenzenesulfonic acids such as 3-propyl-4-methylthiobenzenesulfonic acid, 2-methyl-5-methylthiobenzenesulfonic acid, 3-butyl-4-butylthiobenzenesulfonic acid, and 2-methoxy-4-ethylthiobenzenesulfonic acid; substituted and unsubstituted thiophenesulfonic acids such as 2-thiophenesulfonic acid, 3-butyl-2-thiophenesulfonic acid, 3-ethxoy-2-thiophenesulfonic acid, and 3-phenyl-2-thiophenesulfonic acid; substituted and unsubstituted thiophanesulfonic acids such as 2-thiophanesulfonic acid, 4-phenyl-2-thiophanesulfonic acid, and 3-propoxy-2-thiophanesulfonic acid; phenothiazine; N-substituted and/or ring substituted phenothiazines such as N-ethylphenothiazine, N-acetylphenothiazine, N-formylphenothiazine, 8-methylphenothiazine, 8-methylphenothiazine-3-sulfonic acid, N-formyl-8-ethylphenothiazine, 2-phenothiazine carboxylic acid, 3-phenothiazinesulfonic acid, and N-methyl-4-propoxy-8-phenothiazinesulfonic acid; substituted and unsubstituted thiophenecarboxylic acid such as 2-thiophenecarboxylic acid, 4-phenyl-2-thiophenecarboxylic acid, 4-ethyl-2-thiophenecarboxylic acid, 4-methoxy-2-thiophenecarboxylic acid and 3-propyl-2-thiophenecarboxylic acid; substituted and unsubstituted thiophanecarboxylic acids such as 2-thiophane carboxylic acid, 3-phenyl-2-thiophanecarboxylic acid, and 4-butyl-2-thiophanecarboxylic acid; substituted and unsubstituted alkylthiobenzoic acids such as p-butylthiobenzoic acid, m-ethylthiobenzoic acid and o-methylthiobenzoic acid; ring substituted alkylthiobenzoic acid such as 2-methyl-4-propylthiobenzoic acid and 3-butoxy-4-butylthiobenzoic acid; thiophenyl substituted and substituted thiophenyl substituted lower alkyl carboxylic acids such as 2-thiophenylacetic acid, 3-propyl-2-thiophenylacetic acid, and 4-(4-ethoxy-2-thiophenyl)butyric acid; thiophanyl and substituted thiophanyl substituted lower alkyl carboxylic acids such as 2-thiophanylacetic acid, 4-phenyl-2-thiophanylacetic acid, and 3-(3-methoxy-2-thiophanyl)propanoic acid; phenylthio substituted lower alkyl carboxylic acids such as, for example, phenylthioacetic acid, 3-phenylthiopropanoic acid and 4-phenylthiobutyric acid; and ring substituted phenylthio substituted lower alkyl carboxylic acids such as p-methoxyphenylthioacetic acid, m-propylphenylthioacetic acid and 4-(m-ethoxyphenylthio)butyric acid. Salts of the various sulfonic and carboxylic acids may also be used in the reactor charge but, in the presence of substantial proportions of mineral acids, the carboxylic or sulfonic compound is substantially in acid form during reaction.

Particularly preferred sulfur compounds include the sulfonated alkylthiobenzene compounds corresponding to the formula where $R^1$ is alkyl, $R^2$ is hydrogen, ammonium, or alkali metal and $R^3$ is hydrogen, lower alkyl, lower alkylthio or lower alkoxy; sulfonated thiophenes corresponding to the formula where $R^2$ and $R^3$ are as defined above; sulfonated thiophanes corresponding to the formula where $R^2$ and $R^3$ are as defined above; substituted or unsubstituted phenothiazine corresponding to the formula where $R^4$ is hydrogen, lower alkyl, carbonyl, lower alkyl substituted carbonyl or carboxyl, and $R^5$ and $R^6$ are independently selected from among hydrogen, lower alkyl, lower alkoxy, aryl, sulfonic acid, carboxylic acid, sulfonate salt and carboxylate salt; carboxylated thiophenes corresponding to the formula where $R^7$ is hydrogen, ammonium, or alkali metal and $R^3$ is as defined above; carboxylated thiophanes corresponding to the formula where $R^3$ and $R^7$ are as defined above; thiophenyl substituted sulfonic acids corresponding to the formula where $R^8$ is alkylene having between about 1 and about 4 carbon atoms, and $R^3$ and $R^7$ are as defined above; thiophanyl substituted sulfonic acids corresponding the the formula where $R^3$, $R^7$ and $R^8$ are as defined above; alkylthiobenzoic acids corresponding to the formula where $R^1$, $R^3$, and $R^7$ are as defined above; and phenylthio substituted carboxylic acids corresponding to the formula where $R^7$ and $R^8$ are defined above.

Because of the low volatility and hydrolytic stability of the preferred sulfur compounds, neither the sulfur compound nor its hydrolytic breakdown products accumulate in the vapor space of the reactor, and thus do not detract from the hydrogen pressure available for driving the reaction. High yields are achieved, not only because of the superior selectivity afforded by use of the preferred sulfur compounds, but also by virtue of the fact that the sulfur compounds are essentially inert and do not react with either arylhydroxylamine or mineral acid. Moreover, high product quality is preserved because the sulfur compound is purged in the aqueous stream, neither accumulating in the unreacted nitrobenzene nor appearing in any substantial proportion in the p-aminophenol obtained by precipitation from the acid stream after completion of the rearrangement reaction.

In the preferred embodiment of the invention, only 50% to 90% of the nitrobenzene is reduced in the catalytic hydrogenation. At temperatures adequate for the rearrangement reaction, complete conversion promotes the formation of by-products that poison the catalyst. This effect tends to be aggravated by the presence of the sulfur compound. However, by operating in the 50% to 90% conversion range the aggravating effect of sulfur compound on catalyst poisoning is avoided or minimized.

Figure 1:
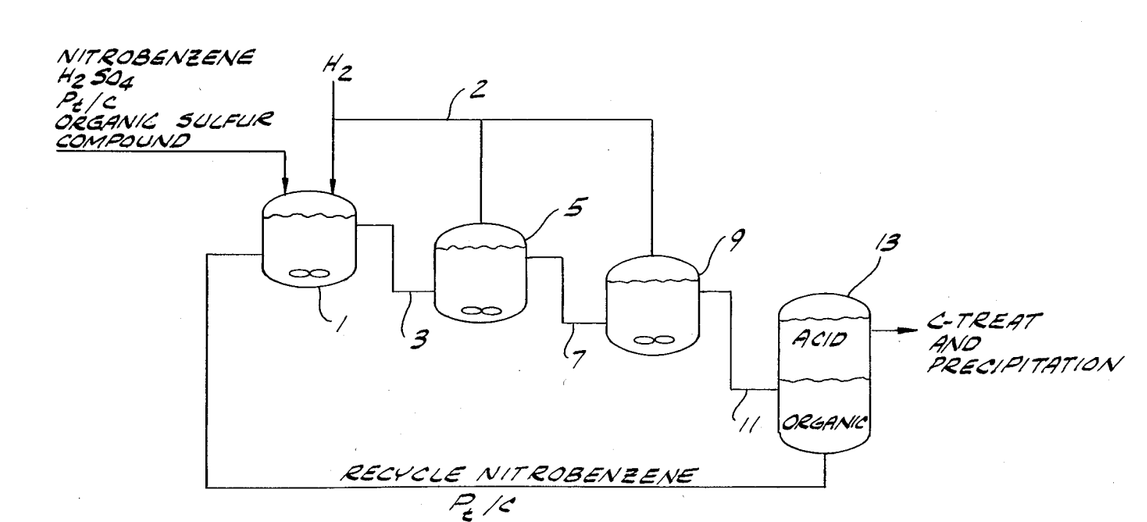

Illustrated in the drawing is a schematic flow sheet of an embodiment in which the process of the invention is carried out continuously in a three hydrogenator cascade system. Fresh nitrobenzene, dilute highly dissociated acid (preferably sulfuric), water, sulfur compound and catalyst are charged to a first hydrogenation reactor 1 along with a recycle stream of unreacted nitrobenzene and a catalyst. A cationic surfactant is also preferably included in the charge mixture. Hydrogen is introduced into reactor 1 via a hydrogen supply line 2 and the hydrogenation reaction is carried out under a hydrogen pressure of 0 to 50 psig by agitation of the mixture contained in the vessel at the temperature in the range of 70° C. to 100° C., preferably 77° C. to 82° C. Nitrobenzene is readily reduced to phenylhydroxylamine but the presence of the sulfur compound inhibits conversion of phenylhydroxylamine to aniline and, as the phenylhydroxylamine is formed, it is absorbed into the aqueous phase. In the presence of the acid, the phenylhydroxylamine rearranges to p-aminophenol. Exothermic reaction heat from the reduction and rearrangement reactions is removed and the reaction temperature controlled by cooling water passed through a jacket, internal coil or external heat exchanger associated with the reactor.

Reacting mixture continuously overflows reactor 1 through a discharge line 3 to a second reactor 5 which is also agitated under hydrogen pressure at a temperature in the aforesaid range. Reduction of nitrobenzene and formation of p-aminophenol continues in reactor 5 and exothermic reaction heat is removed in the same manner as for reactor 1. Because a greater share of the reaction occurs in reactor 1, the cooling load on reactor 5 is significantly lower than for reactor 1. Reacting mixture continuously overflows from reactor 5 through an overflow line 7 into a third reactor 9 where the reaction continues at a rate somewhat below that occurring in reactor 5. The temperature of the reaction mixture in reactor 9 is controlled at approximately the same level as in reactors 1 and 5. Temperature control is provided in essentially the same manner as for the other reactors but, depending on the degree of conversion in the first two reactors, relatively little cooling may be needed in the third reactor.

By coordinated control of fresh nitrobenzene feed rate, catalyst loading, hydrogen pressure and temperature, conversion of nitrobenzene in the reactor system is preferably limited to between about 50% and about 90%. Optimal conversion is typically about 80%.

Reaction mixture overflows continuously from reactor 9 through a discharge pipe 11 into a decant tank 13. In the decant tank, the phases separate, with unreacted nitrobenzene organic phase containing the catalyst settling to the bottom and the aqueous phase containing p-aminophenol and acid rising to the top. Nitrobenzene and catalyst are continuously drawn off the bottom of decant tank 13 and returned to reactor 1. p-Aminophenol liquor (aqueous phase) overflows continuously from the top of decant tank 13 and is subsequently subjected to conventional carbon treatment and precipitation steps for purification and recovery of the final product.

Although sulfuric acid is the preferred agent for the rearrangement reaction, other dilute highly dissociated acids may be used. Benzenesulfonic acid and toluenesulfonic acid are particularly suitable but other acids such as phosphoric acid and trihaloacetic are effective. Hydrogen halide acids are preferably not used.

When sulfuric acid is used, the dilute acid typically has substantially the same composition as disclosed in the Benner patent, i.e., 5% to 20% by weight, preferably 10% to 15% by weight. However, the relative proportions of acid to nitrobenzene may typically differ somewhat from those disclosed by Benner. Preferably, the total charge ratio is between about 0.7 and about 1.2 moles sulfuric acid per mole of nitrobenzene (fresh plus recycled), with approximately 0.9 moles sulfuric acid per mole nitrobenzene being approximately optimum. p-Aminophenol liquor (aqueous phase) leaving the last hydrogenator should contain at least about 5% free acid.

Preferably, the platinum catalyst is provided on a carbon support at a level of approximately 0.5% to 5% by weight. Other acid resistant supports may also be used, but abrasive supports should be avoided when ceramic glass-lined reactors are used. Platinum oxide catalysts are also suitable but platinum metal is preferred.

Catalyst loading is also a parameter of some importance in the process of the invention. Preferably, the charge mixture contains between about $3.0 \times 10^{-5}$ and about $5.0 \times 10^{-4}$ gram-atoms platinum per mole of nitrobenzene substrate.

As indicated above, the sulfur compound is supplied to the process at a rate sufficient to provide a concentration of about 0.1 to about 100 moles, preferably about 0.1 to 10 moles per gram atom of platinum metal. Optimum sulfur compound content varies directly with the molecular weight of the sulfur compound, but essentially always falls within the aforesaid ranges. In a continuous operation such as that described above, the sulfur compound may be added in small increments at regular intervals to provide the approximate amounts needed, and the reaction mixture monitored so that the addition schedule can be modified if the sulfur compound content is moving out of the desired range. Because formation of by-product aniline is essentially eliminated, hydrogen flow to the continuous process adjusts to approximately two moles per mole of fresh nitrobenzene charged to the reaction.

A cationic surfactant is preferably included in the charge mixture to facilitate extraction of phenylhydroxylamine into the aqueous phase. Various quaternary ammonium salts or hydroxides can be used. Typically, the surfactant is present in a proportion of 0.1% to 1% by weight based on the total reaction mass.

As noted above, the process of the invention is useful for the preparation of both unsubstituted and lower alkyl substituted p-aminophenols, by catalytic hydrogenation of the corresponding unsubstituted or substituted nitrobenzene. Thus, generally the substrate used in the reaction may have the formula where R is lower alkyl and n is 0, 1 or 2. Typical of substrates which are useful in the process of the invention are o-nitrotoluene, m-nitrotoluene and 2,6-dimethylnitrobenzene.

Although the process of the invention is advantageously and preferably carried out in a continuous system such as the cascade reactor system illustrated in the drawing, it will be understood that batch systems may also be used. In such event, the nitroaryl substrate, catalyst, acid and sulfur compound are charged to the batch hydrogenator in such amounts as to provide the proportions referred to above. After reaction is carried to the desired conversion, the batch is blown or pumped to a decant tank where the nitroaryl phase containing the catalyst separates from the aqueous phase containing the p-aminophenol. Nitroaryl substrate and catalyst are recycled to the reactor and the aqueous phase is subjected to further conventional treatment for purification and recovery of the p-aminophenol product.

The following examples illustrate the invention.

EXAMPLE 1

Nitrobenzene was converted to p-aminophenol by catalytic hydrogenation in the presence of dilute sulfuric acid, using a 1 liter Morton flask fitted with an agitator, thermometer, reflux condenser and low pressure nitrogen and hydrogen feed lines.

A charge mixture was prepared by adding the following components, in the order given, to the Morton flask:
Nitrobenzene (57 ml)
Deionized water (406 ml)
Concentrated sulfuric acid (27 ml)
3% platinum on carbon catalyst, 70% wet (2.0 grams)
Arquad 12-33 (dodecyltrimethylammonium chloride cationic surfactant) (30% solution in isopropanol) (1.71 ml)
Diethyl sulfide (0.00846 grams)

After the charge mixture was prepared in the flask, the flask was purged with nitrogen and then with hydrogen. The charge mixture was then heated under mild agitation to a temperature of 80° C. after which the agitator speed was increased and hydrogen absorption began. Hydrogen pressure was maintained at approximately 5 inches water and the temperature was controlled at 78° C. to 82° C. throughout the reaction period. After three hours, approximately 75% of the nitrobenzene had reacted, at which point the reaction was terminated and the reactor flask purged with nitrogen.

To facilitate yield determination, the catalyst was recovered by filtration, and the filtered reaction mixture thereafter placed in a separatory funnel where the organic and aqueous phases were allowed to separate. The unreacted nitrobenzene organic phase was removed and weighed. The aqueous phase was neutralized with ammonia to a pH of 7.5-8.0, thereby precipitating the p-aminophenol product. This product was recovered by filtration, washed and dried for yield determination. Nitrobenzene conversion was calculated by subtracting the weight of unreacted nitrobenzene from the nitrobenzene charge and dividing by the latter. Selectivity of the diethyl sulfide modified catalyst system was determined by dividing the moles of p-aminophenol formed by the moles of nitrobenzene consumed, and multiplying by 100. Taking into consideration known solubility losses, selectivity of the reaction was determined to be about 78.9% at a conversion of 75%.

To provide a basis of comparison, another reaction was carried out in substantially the same way as described above except that no sulfur compound additive was included in the charge mixture. At a nitrobenzene conversion of 69.2%, selectivity for p-aminophenol was determined to be only 68.2%.

EXAMPLE 2

Using the apparatus and method generally described in Example 1, a series of catalytic hydrogenations was carried out at 80° C. for conversion of nitrobenzene to p-aminophenol. In the first run of this series no catalyst modifer was used while, in the other runs, various divalent sulfur compounds were employed in varying amounts as catalyst modifiers. The reaction mixture was worked up in essentially the same way as in Example 1 and the conversion, selectivity and p-aminophenol productivity were determined. The results of the runs of this Example are set forth in Table I.

TABLE I

| | At 80° C. | | | | |
|---|---|---|---|---|---|
| Catalyst Modifier | Modifier Moles g-atom Pt. | Conversion | Selectivity | g's PAP hr. | Time |
| None | — | 69.2% | 68.2% | 9.54 | 180 min. |
| (CH$_3$)$_2$S | 16.9 | 33.3 | 71.7 | 4.58 | 190 min. |

TABLE I-continued

| | At 80° C. | | | | |
|---|---|---|---|---|---|
| Catalyst Modifier | Modifier Moles g-atom Pt. | Conversion | Selectivity | g's PAP hr. | Time |
| $(C_2H_5)_2S$ | 1.0 | 74.6 | 78.9 | 11.92 | 180 min. |
| dl-methionine | 0.5 | 80.8 | 72.1 | 11.76 | 180 min. |
| $(C_2H_5)_2S$ | 9.2 | No reaction | | | |

EXAMPLE 3

Using the apparatus and method generally described in Example 1, another series of catalytic hydrogenations of nitrobenzene to p-aminophenol was carried out at 95° C. In one of these runs, no sulfide compound was used while, in the others, a divalent sulfur compound was incorporated in the charge mixture to enhance catalyst selectivity. Results of the runs of this Example are set forth in Table II.

TABLE II

| | At 95° C. | | | | |
|---|---|---|---|---|---|
| Catalyst Modifier | Modifier Moles g-atom Pt. | Conversion | Selectivity | g's PAP hr. | Time |
| $(CH_3)_2S$ | 1.2 | 28.4% | 79.2% | 4.55 | 180 min. |
| $(C_2H_5)_2S$ | 1.0 | 27.2 | 87.7 | 4.81 | 180 min. |
| None | — | 35.6 | 74.0 | 4.92 | 195 min. |

EXAMPLE 4

Using the apparatus and method generally described in Example 1, a series of catalytic hydrogenations was carried out at 80° C. for conversion of nitrobenzene to p-aminophenol. The charged mixture contained:
Nitrobenzene (57 ml)
Deionized water (406 ml)
98% sulfuric acid (27 ml)
3% platinum on carbon catalyst, 70% wet (2.0 g)
50% active trimethyldodecylammonium chloride sold under the trade designation "Arquad 12-50" by Armak (1.5 ml)
Divalent sulfur compound (See Table III)
Sulfur compounds used in the runs of this example included 2-thiophenecarboxylic acid, 2-thiopheneacetic acid, phenothiazine and a p-methylthiobenzoic acid. In addition, two control reactions were run in the absence of any sulfur compounds. Set forth in Table III are data on the catalyst modifier loading and the conversion and selectivity obtained, together with data on the melting points and boiling points of the sulfur compounds used.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A process for the preparation of substituted or unsubstituted p-aminophenol having the formula where R is lower alkyl and n is 0, 1 or 2, the process comprising the steps of:
preparing a charge mixture comprising a substrate comprising a substituted or unsubstituted nitrobenzene having the formula where R and n are as defined above, a highly dissociated acid, a catalyst containing platinum, and a divalent sulfur compound in which sulfur is bonded to two other moieties, said sulfur compound being present in a proportion of between about 0.1 and about 100 moles per gram atom of platinum, said mixture comprising an organic phase containing said substrate and an aqueous phase containing said acid;
introducing hydrogen into the mixture at a pressure of between about 0 and about 50 psig while agitating said mixture at a temperature between about 70° C. and about 100° C., thereby causing said substrate to be reduced to a hydroxylamine having the formula

TABLE III

| DIVALENT SULFUR COMPOUND | LOADING moles S-cmpd g-atom Pt. | SELECTIVITY moles PAP/ moles NB consumed (100) | CONVERSION (100) moles NB consumed/ moles NB charged | PROPERTIES OF CATALYST MODIFIERS | |
|---|---|---|---|---|---|
| | | | | Melting Point | Boiling Point |
| Standard - None | 0 | 74.4 | 20.2 | | |
| Standard - None | 0 | 71.3 | 80.6 | | |
| 2-Thiophene-Carboxylic Acid | 0.50 | 84.6 | 58.8 | 63° C.–67° C. | 160° C. at 22 mm Hg |
| 2-Thiophene-Acetic Acid | 1.00 | 84.1 | 38.2 | 127° C.–130° C. | 260° C. |
| Phenothiazine | 0.27 | 88.3 | 40.9 | 180° C.–185° C. | 371° C. |
| p-Methylthio-benzoic Acid | 0.50 | 89.0 | 22.5 | 185° C.–188° C. | | where R and n are as defined above, said hydroxylamine being rearranged in the presence of said acid to produce said substituted or unsubstituted p-aminophenol; and recovering the p-aminophenol product from the aqueous phase.

2. A process as set forth in claim 1 wherein said sulfur compound is selected from the group consisting of dialkyl sulfides, diaryl sulfides, aryl alkyl sulfides, thiophene, substituted thiophenes, thiophane, substituted thiophanes and methionine.

3. A process as set forth in claim 2 wherein said sulfur compound comprises methionine.

4. A process as set forth in claim 1 wherein said sulfur compound has a boiling point of at least about 80° C. and is hydrolytically stable and nonreactive with arylhydroxylamines under the conditions of the catalytic hydrogenation of nitrobenzene or substituted nitrobenzene.

5. A process as set forth in claim 4 wherein the sulfur compound is distributed predominantly in the aqueous acid phase rather than the organic phase.

6. A process as set forth in claim 5 wherein said sulfur compound is selected from the group consisting of alkylthiobenzenesulfonic acids and salts thereof, ring substituted alkylthiobenzenesulfonic acids, thiophenesulfonic acids and salts thereof, substituted thiophenesulfonic acids and salts thereof, thiophanesulfonic acids and salts thereof, phenothiazine, N-substituted phenothiazines, ring substituted phenothiazines, thiophenecarboxylic acids and salts thereof, ring substituted thiophenecarboxylic acids and salts thereof, thiophanecarboxylic acids and salts thereof, ring substituted thiophanecarboxylic acids and salts thereof, thiophenyl substituted lower alkyl carboxylic acids and salts thereof, ring substituted thiophenyl substituted lower alkyl carboxylic acids and salts thereof, thiophanyl substituted lower alkyl carboxylic acids and salts thereof, ring substituted thiophanyl substituted lower alkyl carboxylic acids and salts thereof, alkylthiobenzoic acid and salts thereof, ring substituted alkylthiobenzoic acids and salts thereof, phenylthio substituted lower alkyl carboxylic acids and salts thereof, and ring substituted phenylthio substituted lower alkyl carboxylic acids and salts thereof.

7. A process as set forth in claim 6 wherein said sulfur compound is selected from the group consisting of sulfonated alkythiobenzenes corresponding to the formula where $R^1$ is alkyl, $R^2$ is selected from the group consisting of hydrogen, ammonium, and alkali metal, and $R^3$ is selected from the group consisting of hydrogen, lower alkyl, lower alkoxy and lower alkylthio, sulfonated thiophenes corresponding to the formula where $R^2$ and $R^3$ are as defined above, sulfonated thiophanes corresponding to the formula where $R^2$ and $R^3$ are as defined above, phenothiazine and substituted phenothiazines corresponding to the formula where $R^4$ is selected from the group consisting of hydrogen, lower alkyl, carbonyl, lower alkyl substituted carbonyl and carboxyl, and each of $R^5$ and $R^6$ independently selected from the group consisting of hydrogen, alkyl, aryl, alkoxy, alkylthio, sulfonic acid, carboxylic acid, sulfonate salt and carboxylate salt, carboxylated thiophenes corresponding to the formula where $R^7$ is selected from the group consisting of hydrogen, ammonium, and alkali metal and $R^3$ is as defined above, carboxylated thiophanes corresponding to the formula where $R^3$ and $R^7$ are as defined above, thiophenyl substituted sulfonic acids corresponding to the formula where $R^8$ is alkylene having between one and about 4 carbon atoms and $R^3$ and $R^7$ are as defined above, thiophanyl substituted sulfonic acids corresponding to the formula where R³, R⁷, and R⁸ are as defined above, alkylthiobenzoic acids corresponding to the formula where R¹, R³ and R⁷ are as defined above, phenylthio substituted carboxylic acids corresponding to the formula where R⁷ and R⁸ are as defined above, and thiophane acetic acid.

8. A process as set forth in claim 7 wherein said sulfur compound is selected from the group consisting of phenothiazine, 2-thiopheneacetic acid, 2-thiophenecarboxylic acid and p-methylthiobenzoic acid.

9. A process as set forth in claim 1 wherein the hydrogenation reaction is terminated after a reduction of between about 50% and about 90% of the substrate contained in the charge mixture, and the aqueous phase containing the substituted or unsubstituted p-aminophenol product is separated from the organic phase containing the catalyst and unreacted substrate.

10. A process as set forth in claim 9 wherein the organic phase containing catalyst and unreacted substrate is recycled and mixed with additional amounts of substrate, dilute acid solution and sulfur compound to provide a charge mixture subject to further hydrogenation.

11. A process as set forth in claim 10 wherein said acid, said substrate and said catalyst are continuously introduced into a hydrogenation vessel and the products of the hydrogenation reaction are continuously removed therefrom.

12. A process as set forth in claim 11 wherein the hydrogenation reaction is carried out in a plurality of hydrogenation vessels arranged in series.

13. A process as set forth in claim 12 wherein the reaction mixture discharged from the last of said series of hydrogenation vessels is transferred to a separation vessel where said aqueous phase and said organic phase are continuously separated and said organic phase is continuously returned to the first of said series of hydrogenation vessels.

14. A process as set forth in claim 9 wherein said charge mixture contains between about 0.1 and about 10 moles sulfur compound per gram atom of platinum.

15. A process as set forth in claim 1 wherein said acid is selected from the group consisting of sulfuric acid, phosphoric acid, trihaloacetic acid, benzenesulfonic acid and toluenesulfonic acid.

16. A process as set forth in claim 15 wherein said acid comprises sulfuric acid.

17. A process as set forth in claim 16 wherein said charge mixture initially contains between about 0.7 and about 1.2 moles sulfuric acid per mole of substrate.

18. A process as set forth in claim 1 wherein said substrate is selected from the group consisting of nitrobenzene, o-nitrotoluene, m-nitrotoluene and 2,6-dimethylnitrobenzene.

* * * * *

UNITED STATES PATENT AND TRADEMARK OFFICE
CERTIFICATE OF CORRECTION

PATENT NO. : 4,571,437
DATED : February 18, 1986
INVENTOR(S) : Douglas C. Caskey and Douglas W. Chapman It is certified that error appears in the above—identified patent and that said Letters Patent is hereby corrected as shown below:

Column 14, claim 7, line 35, "$R^6$ independently" should read -- $R^6$ is independently --. Column 15, claim 7, line 30, "thiophane" should read -- thiophene --.

Signed and Sealed this

Fourteenth Day of October, 1986

[SEAL]

Attest:

DONALD J. QUIGG

*Attesting Officer*   *Commissioner of Patents and Trademarks*